(12) United States Patent
DeVries

(10) Patent No.: US 12,300,361 B2
(45) Date of Patent: May 13, 2025

(54) SYSTEMS AND METHODS FOR INDEPENDENT ASSESSMENT OF IMAGE DATA

(71) Applicant: MERATIVE US L.P., Ann Arbor, MI (US)

(72) Inventor: Jon T. DeVries, Cary, NC (US)

(73) Assignee: Merative US L.P., Ann Arbor, MI (US)

( * ) Notice: Subject to any disclaimer, the term of this patent is extended or adjusted under 35 U.S.C. 154(b) by 425 days.

(21) Appl. No.: 17/540,920

(22) Filed: Dec. 2, 2021

(65) Prior Publication Data
US 2022/0093222 A1 Mar. 24, 2022

Related U.S. Application Data

(60) Continuation of application No. 16/162,663, filed on Oct. 17, 2018, now abandoned, which is a division of application No. 13/650,370, filed on Oct. 12, 2012, now Pat. No. 10,140,420.

(60) Provisional application No. 61/546,373, filed on Oct. 12, 2011.

(51) Int. Cl.
*G16H 10/20* (2018.01)
*G16H 30/20* (2018.01)
*G16H 30/40* (2018.01)
*G16Z 99/00* (2019.01)

(52) U.S. Cl.
CPC ............ *G16H 10/20* (2018.01); *G16H 30/20* (2018.01); *G16H 30/40* (2018.01); *G16Z 99/00* (2019.02)

(58) Field of Classification Search
CPC ..... G06F 19/321; G06F 19/322; G06Q 50/22; G06Q 50/24; H04L 67/12
See application file for complete search history.

(56) References Cited

U.S. PATENT DOCUMENTS

| | | |
|---|---|---|
| 5,040,142 A | 8/1991 | Mori et al. |
| 5,583,758 A | 12/1996 | McIlroy et al. |
| 5,606,609 A | 2/1997 | Houser et al. |
| 5,740,428 A | 4/1998 | Mortimore et al. |
| 5,835,601 A | 11/1998 | Shimbo et al. |
| 5,890,177 A | 3/1999 | Moody et al. |

(Continued)

FOREIGN PATENT DOCUMENTS

WO 96/25719 A2 8/1996

OTHER PUBLICATIONS

Erickson BJ, Buckner JC. Imaging in clinical trials. Cancer Inform. 2007;4: 13-8. Epub May 12, 2007. PMID: 19390660; PMCID: PMC2666946. (Year: 2007).*

(Continued)

*Primary Examiner* — Gandhi Thirugnanam
(74) *Attorney, Agent, or Firm* — Michael Best & Friedrich LLP

(57) ABSTRACT

Systems and methods for managing at least one medical image that includes image data and metadata. One method includes generating, at a processor, a number of copies of the at least one medical image, wherein the number of copies is equal to a number of independent reviewers associated with the at least one medical image. Each of the copies includes the image data and the metadata. The method also includes modifying the metadata of each of the copies to include a unique identifier, and storing the copies to at least one image storage device.

20 Claims, 4 Drawing Sheets

(56) References Cited

U.S. PATENT DOCUMENTS

| | | | |
|---|---|---|---|
| 5,982,956 A | 11/1999 | Lahmi | |
| 6,067,551 A | 5/2000 | Brown et al. | |
| 6,175,426 B1 | 1/2001 | Hirooka | |
| 6,417,870 B1 | 7/2002 | Brackett et al. | |
| 6,519,632 B1 | 2/2003 | Brackett et al. | |
| 6,618,060 B1 | 9/2003 | Brackett | |
| 7,089,247 B2 | 8/2006 | Kloos et al. | |
| 7,102,773 B1 | 9/2006 | Oosterhout et al. | |
| 7,283,857 B1 | 10/2007 | Fallon et al. | |
| 7,383,462 B2 | 6/2008 | Osaki et al. | |
| 7,593,918 B2 | 9/2009 | Gentles et al. | |
| 7,707,043 B2 | 4/2010 | Kuth et al. | |
| 7,783,072 B2 | 8/2010 | Work et al. | |
| 7,854,383 B2 | 12/2010 | Suzuki | |
| 7,860,287 B2 | 12/2010 | Zahlmann et al. | |
| 7,885,825 B2 | 2/2011 | Climax et al. | |
| 8,005,921 B2 | 8/2011 | Ho et al. | |
| 8,086,077 B2 | 12/2011 | Eichhorn | |
| 8,099,307 B2 | 1/2012 | Maresh et al. | |
| 8,140,350 B2 | 3/2012 | Rothpearl et al. | |
| 8,200,505 B2 | 6/2012 | Walker et al. | |
| 8,417,666 B2 | 4/2013 | Bailor et al. | |
| 8,626,524 B1* | 1/2014 | Koehl | H04L 51/08 |
| | | | 705/2 |
| 8,825,594 B2 | 9/2014 | Skaria et al. | |
| 9,354,769 B1* | 5/2016 | Kudva | H04L 12/1822 |
| 10,140,420 B2 | 11/2018 | DeVries | |
| 2001/0051881 A1 | 12/2001 | Filler | |
| 2002/0016718 A1 | 2/2002 | Rothschild et al. | |
| 2002/0023172 A1 | 2/2002 | Gendron et al. | |
| 2002/0191205 A1 | 12/2002 | Stringham | |
| 2003/0208378 A1 | 11/2003 | Thangaraj et al. | |
| 2004/0001606 A1 | 1/2004 | Levy | |
| 2004/0068516 A1* | 4/2004 | Lee | G06F 16/182 |
| 2004/0071038 A1 | 4/2004 | Sterritt | |
| 2004/0085354 A1* | 5/2004 | Massand | H04L 67/10 |
| | | | 707/E17.008 |
| 2004/0143171 A1 | 7/2004 | Kalies | |
| 2004/0143594 A1 | 7/2004 | Kalies | |
| 2004/0176986 A1 | 9/2004 | Kuth et al. | |
| 2005/0044492 A1 | 2/2005 | Ramaley et al. | |
| 2005/0165623 A1 | 7/2005 | Landi et al. | |
| 2005/0185204 A1 | 8/2005 | Shelton et al. | |
| 2005/0256392 A1 | 11/2005 | Matory et al. | |
| 2006/0026034 A1 | 2/2006 | Yankelevitz et al. | |
| 2006/0064328 A1 | 3/2006 | Datta et al. | |
| 2006/0159325 A1 | 7/2006 | Zeineh et al. | |
| 2006/0168338 A1 | 7/2006 | Bruegl et al. | |
| 2006/0177114 A1 | 8/2006 | Tongdee et al. | |
| 2006/0195339 A1 | 8/2006 | Backhaus et al. | |
| 2006/0242144 A1 | 10/2006 | Esham et al. | |
| 2006/0253487 A1 | 11/2006 | O'Blenis | |
| 2006/0259783 A1 | 11/2006 | Work et al. | |
| 2006/0282447 A1 | 12/2006 | Hollebeek | |
| 2007/0035759 A1 | 2/2007 | Fujimori | |
| 2007/0046649 A1 | 3/2007 | Reiner | |
| 2007/0100226 A1 | 5/2007 | Yankelevitz et al. | |
| 2007/0191721 A1 | 8/2007 | Parker | |
| 2007/0216913 A1 | 9/2007 | Toda | |
| 2007/0239782 A1 | 10/2007 | Schneider | |
| 2007/0271316 A1 | 11/2007 | Hollebeek | |
| 2007/0283420 A1 | 12/2007 | Rantalahti | |
| 2007/0291978 A1 | 12/2007 | Kim et al. | |
| 2007/0292012 A1 | 12/2007 | Brandon et al. | |
| 2008/0031459 A1* | 2/2008 | Voltz | H04L 9/083 |
| | | | 380/279 |
| 2008/0052112 A1 | 2/2008 | Zahlmann et al. | |
| 2008/0059241 A1 | 3/2008 | Zahlmann et al. | |
| 2008/0071575 A1 | 3/2008 | Climax et al. | |
| 2008/0117451 A1* | 5/2008 | Wang | H04L 65/40 |
| | | | 358/1.15 |
| 2008/0175484 A1 | 7/2008 | Hartmann et al. | |
| 2008/0175515 A1 | 7/2008 | Hartmann et al. | |
| 2008/0198423 A1 | 8/2008 | Ando et al. | |
| 2008/0201709 A1* | 8/2008 | Hodges | G06F 9/45537 |
| | | | 718/1 |
| 2009/0019360 A1 | 1/2009 | Lynggaard et al. | |
| 2009/0106331 A1 | 4/2009 | Fridman et al. | |
| 2009/0132285 A1* | 5/2009 | Jakobovits | G06F 3/0482 |
| | | | 726/17 |
| 2009/0138318 A1 | 5/2009 | Hawkins et al. | |
| 2009/0226056 A1 | 9/2009 | Vlachos et al. | |
| 2009/0282006 A1* | 11/2009 | Misvaer | G06Q 10/06 |
| 2009/0287504 A1* | 11/2009 | Benjamin | G16H 40/67 |
| | | | 705/2 |
| 2010/0021027 A1 | 1/2010 | Hartkens et al. | |
| 2010/0034376 A1 | 2/2010 | Okuizumi et al. | |
| 2010/0131873 A1 | 5/2010 | Mejia et al. | |
| 2010/0228699 A1 | 9/2010 | Webber et al. | |
| 2010/0250285 A1* | 9/2010 | Shelton | G06F 21/6254 |
| | | | 715/764 |
| 2011/0022414 A1* | 1/2011 | Ge | G16H 30/20 |
| | | | 705/3 |
| 2011/0059432 A1 | 3/2011 | Ballhause et al. | |
| 2011/0093481 A1 | 4/2011 | Hussam | |
| 2011/0110568 A1 | 5/2011 | Vesper et al. | |
| 2011/0153351 A1 | 6/2011 | Vesper et al. | |
| 2011/0153361 A1 | 6/2011 | Hanina | |
| 2012/0105632 A1* | 5/2012 | Renkis | G08B 13/1966 |
| | | | 348/143 |
| 2012/0143617 A1* | 6/2012 | Connors | G16H 10/20 |
| | | | 705/2 |
| 2012/0224742 A1 | 9/2012 | Musser, Jr. | |
| 2012/0259710 A1* | 10/2012 | Peterson | G06Q 30/0241 |
| | | | 705/14.72 |
| 2012/0302212 A1 | 11/2012 | Ross et al. | |
| 2013/0094728 A1 | 4/2013 | DeVries | |
| 2013/0103425 A1 | 4/2013 | Julsrud | |
| 2013/0185098 A1 | 7/2013 | Mitchel et al. | |
| 2013/0346104 A1 | 12/2013 | Pillai | |
| 2014/0112447 A1 | 4/2014 | Semba | |
| 2014/0142983 A1 | 5/2014 | Backhaus et al. | |
| 2014/0222444 A1 | 8/2014 | Cerello et al. | |
| 2014/0297309 A1 | 10/2014 | Kim et al. | |
| 2014/0350962 A1 | 11/2014 | Robinson | |
| 2014/0379639 A1 | 12/2014 | Gasser et al. | |
| 2016/0092943 A1* | 3/2016 | Vigier | H04W 4/021 |
| | | | 705/346 |

OTHER PUBLICATIONS

Brown MS, Pais R, Qing P, Shah S, McNitt-Gray MF, Goldin JG, Petkovska I, Tran L, Aberle DR. An architecture for computer-aided detection and radiologic measurement of lung nodules in clinical trials. Cancer Inform. 2007;4:25-31. Epub May 12, 2007. PMID: 19390662; PMCID: PMC2666948. (Year: 2007).*

R. Martinez, Y. Alsafadi and J. Kim, "Design of multimedia global PACS distributed computing environment," Proceedings of the Twenty-Eighth Annual Hawaii International Conference on System Sciences, Wailea, HI, USA, 1995, pp. 461-469 vol.3, doi: 10.1109/HICSS.1995.375629 (Year: 1995).*

Oct. 17, 2018, U.S. Appl. No. 16/162,663, 2019-0051402.

Oct. 12, 2012, U.S. Appl. No. 13/650,370, U.S. Pat. No. 10,140,420.

A. L. Belton et al., "Tumour Size Measurement in an Oncology Clinical Trial: Comparison Between Off-site and On-site Measurements", 2003, Clinical Radiology 58, p. 311-314.

Author Unknown, DICOM PS3.3 2021b—Information Object Definitions, http://dicom.nema.org/medical/dicom/current/output/chtml/part03/sect_C.17.2.2.html (Year: 2001).

https://www.inspire.com/groups/talk-psoriasis/discussion/protocol-when-two-specialists-disagree/?ga=freshen, Protocol when two Specialists disagree, author unknown, Sep. 11, 2013, p. 1-18.

Kevin O'Donnell, Imaging Object Change Management—Detailed Proposal, https://wiki.ihe.net/index.php/Imaging_Object_Change_Management_-_Detailed_Proposal (Year: 2009).

Kinson Ho, Basic Imaging Object Change Management—Detailed Proposal, https://wiki.ihe.net/index.php/Basic_Imaging_Object_Change_Management_Detailed_Proposal (Year: 2010).

(56) References Cited

OTHER PUBLICATIONS

Oleg, "Digital Imaging and Communications in Medicine (DICOM) A practical Introduction and Survival Guide," Springer-Verlag Berlin Heidelberg, p. 1-424 (Year 2012).
Wang, Fusheng et al., "Towards Building High Performance Medical Image Management System for Clinical Trials", May 20, 2011, Proc SPIE 2011, p. 1-14.
Restriction Requirement from the U.S. Patent and Trademark Office for U.S. Appl. No. 13/650,370 dated Feb. 18, 2015 (6 pages).
Non-Final Office Action from the U.S. Patent and Trademark Office for U.S. Appl. No. 13/650,370 dated Jun. 3, 2015 (19 pages).
Final Office Action from the U.S. Patent and Trademark Office for U.S. Appl. No. 13/650,370 dated Jan. 14, 2016 (26 pages).
Applicant-Initiated Interview Summary from the U.S. Patent and Trademark Office for U.S. Appl. No. 13/650,370 dated Apr. 18, 2016 (3 pages).
Non-Final Office Action from the U.S. Patent and Trademark Office for U.S. Appl. No. 13/650,370 dated Aug. 10, 2016 (27 pages).
Final Office Action from the U.S. Patent and Trademark Office for U.S. Appl. No. 13/650,370 dated Feb. 23, 2017 (34 pages).
Non-Final Office Action from the U.S. Patent and Trademark Office for U.S. Appl. No. 13/650,370 dated Jan. 11, 2018 (33 pages).
Notice of Allowance from the U.S. Patent and Trademark Office for U.S. Appl. No. 13/650,370 dated Jul. 19, 2018 (9 pages).
Non-Final Office Action from the U.S. Patent and Trademark Office for U.S. Appl. No. 16/162,663 dated May 20, 2020 (12 pages).
Applicant-Initiated Interview Summary from the U.S. Patent and Trademark Office for U.S. Appl. No. 16/162,663 dated Aug. 10, 2020 (3 pages).
Final Office Action from the U.S. Patent and Trademark Office for U.S. Appl. No. 16/162,663 dated Oct. 21, 2020 (14 pages).
Non-Final Office Action from the U.S. Patent and Trademark Office for U.S. Appl. No. 16/162,663 dated May 24, 2021 (16 pages).
Final Office Action from the U.S. Patent and Trademark Office for U.S. Appl. No. 16/162,663 dated Oct. 28, 2021 (23 pages).

* cited by examiner

SYSTEMS AND METHODS FOR INDEPENDENT ASSESSMENT OF IMAGE DATA

RELATED APPLICATIONS

This application is a continuation application of U.S. patent application Ser. No. 16/162,663 filed Oct. 17, 2018, which is a divisional application of U.S. patent application Ser. No. 13/650,370 filed Oct. 12, 2012, which claims priority to U.S. Provisional Patent Application No. 61/546,373, filed Oct. 12, 2011. The entire content of all prior-filed applications is hereby incorporated by reference.

BACKGROUND

The present invention relates to digital image processing systems and methods. In particular, the invention relates to digital image processing systems and methods for managing medical images.

SUMMARY

Medical images can be acquired for various reasons and uses. Medical images can be acquired for diagnostic and treatment purposes within a hospital setting. In particular, a physician may request that a patient undergo a radiological examination so that the physician can diagnose the patient or track the progress or treatment of a previously-diagnosed issue. In this context, after the images are initially acquired, the images are reviewed by the physician or other healthcare professionals (e.g., a radiologist). The reviewer uses an image viewer to assess the images and make measurements and annotations associated with the images. The reviewer also provides a report summarizing his or her findings, which often includes a dictated narrative. The measurements, annotations, and report are stored and associated with the acquired images. Therefore, if the acquired images are later accessed (e.g., as part of a "second" review or as a standard part of reviewing a patient's health record), the original reviewer's measurements, annotations, and report are available. Making this information available to subsequent reviewers aids informed treatment of a patient based on all available information.

Medical images can also be acquired as part of a clinical trial. For example, during a clinical trial for a new cancer drug, trial participants may undergo one or more radiological examinations to determine how a cancerous tumor reacts to the new drug. Images acquired during a clinical trial are typically handled differently than images acquired in a hospital setting. First, as compared to the non-standard, narrative report generated by a reviewer in a hospital setting, a reviewer in a clinical trial provides an objective quantitative analysis that relies on evidence-based measurements, such as biomarkers. To ensure the accuracy of these objective observations and measurements, images acquired as part of a clinical trial are often blindly reviewed (e.g., in tandem) by at least two reviewers. The results from the reviewers are compared to determine whether the results match. If the results match, the independent assessments are saved for subsequent use and/or review. If the results do not match, one or more additional reviewers may be used to evaluate the images as a tie-breaker. In the end, all of the independent assessments are saved for subsequent use and/or review.

Because images in a clinical trial need to be reviewed blindly by multiple reviewers, systems and methods used to analyze images in a hospital setting are often unusable for clinical trials or require extensive (and costly) modification. Accordingly, many clinical trials rely on manual processes to manage images, which are slow, inefficient, and prone to human errors. Accordingly, embodiments of the invention provide systems and methods for managing image assessment within a clinical trial setting.

In one embodiment, the invention provides a method for managing at least one medical image. The method includes receiving information regarding the at least one medical image, and determining, at a first processor, a number of copies needed of the at least one medical image based on the information regarding the at least one medical image. The method also includes generating, at the first processor, a unique identifier for each copy and providing, to a second processor, the number of copies needed and the unique identifiers. The second processor generates the number of copies of the at least one medical image, modifies each of the copies based on one of the unique identifiers, and stores the copies to at least one image storage device.

In another embodiment, the invention provides a method for managing at least one medical image, wherein the at least one medical image includes image data and metadata. The method includes generating, at a processor, a number of copies of the at least one medical image, wherein the number of copies is equal to a number of independent reviewers associated with the at least one medical image and each of the copies includes the image data and the metadata. The method also includes modifying the metadata of each of the copies to include a unique identifier, and storing the copies to at least one image storage device.

In yet another embodiment, the invention provides a system for managing at least one medical image. The system includes a first processor configured to receive information regarding the at least one medical image, wherein the at least one medical image includes image data and metadata, and to determine a number of copies needed of the at least one medical image based on the information regarding the at least one medical image. The first processor is also configured to generate a number of unique identifiers, the number of unique identifiers equal to the number of copies needed, and to provide, to a second processor, the number of copies needed and the unique identifiers. The second processor generates the number of copies of the at least one medical image, modifies each of the copies to include one of the unique identifiers, and stores the copies to at least one image storage device.

Other aspects of the invention will become apparent by consideration of the detailed description and accompanying drawings.

DETAILED DESCRIPTION

Figure 1:
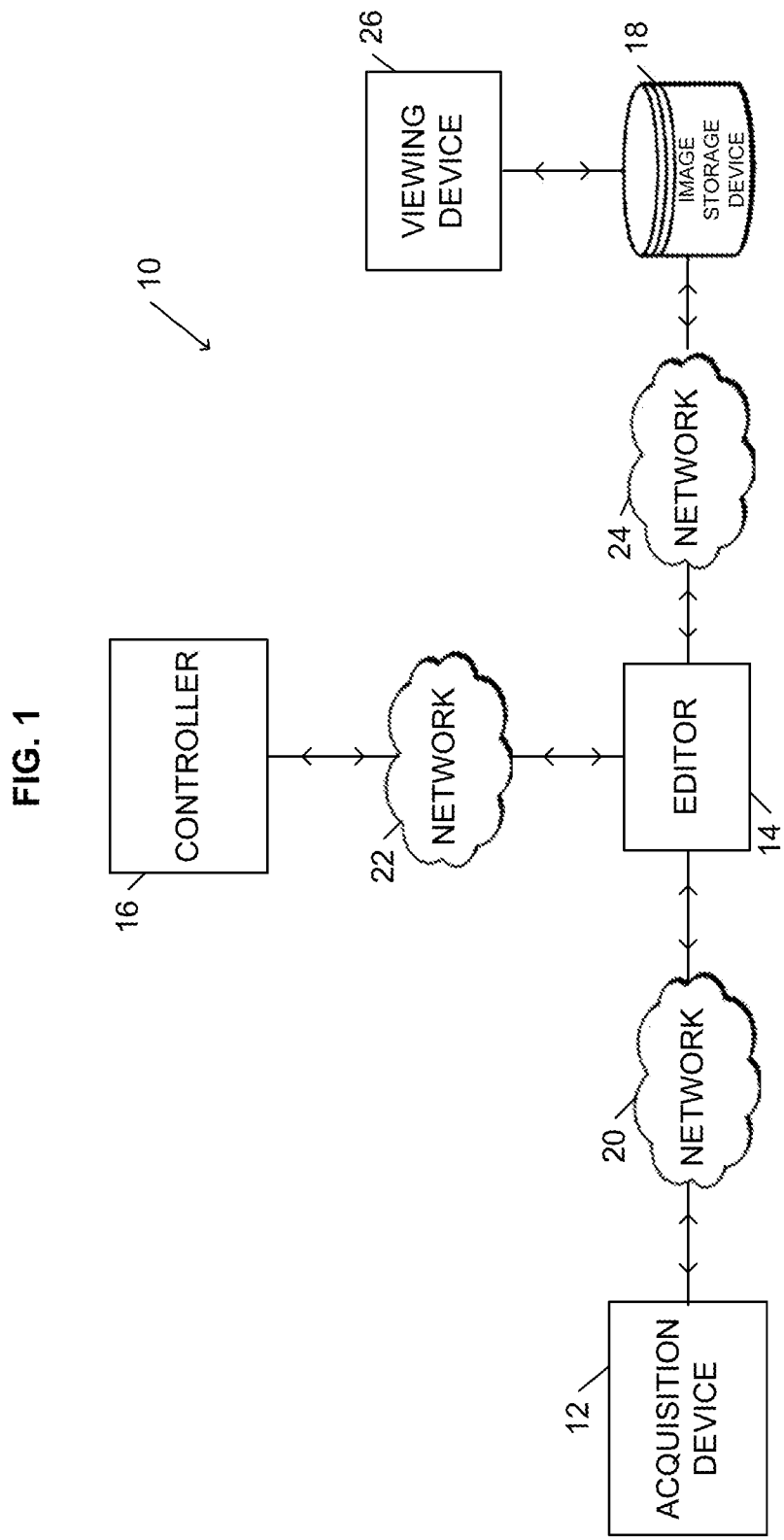
FIG. 1 illustrates a digital image processing system according to one embodiment of the invention.

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways. It should also be noted that a plurality of hardware and software based devices, as well as a plurality of different structural components may be utilized to implement the invention. Furthermore, and as described in subsequent paragraphs, the specific configurations illustrated in the drawings are intended to exemplify embodiments of the invention and that other alternative configurations are possible.

As described above in the summary section, medical images are used and assessed differently in hospital settings than in clinical trial settings. Within the hospital setting, numerous systems and methods have been developed that match the way images are used and processed. For example, hospitals and other image acquisition sites and networks typically use (1) a Radiology Information System ("RIS") that stores and manages billing, image reports, scheduling, etc. associated with radiological examinations and (2) a Picture Archiving and Communication System ("PACS") that stores and manages the images associated with the radiological examinations. The RIS runs in parallel with the PACS in a streamlined, linear process that automates the standard process of assessing images in a hospital setting. As noted above, the PACS allows individuals to access stored images and any associated annotations, measurements, or reports for a particular radiological examination or a particular patient. Accordingly, as previously noted, although clinical trials also assess medical images, clinical trials often cannot use the standard products and systems used in a hospital setting.

FIG. 1 illustrates a digital image processing system 10. The system 10 can be used to manage images acquired for a clinical trial. The system 10 includes one or more acquisition devices 12, an editor 14 (e.g., a digital imaging and communications in medicine ("DICOM") editor), a controller 16, and an image storage device 18. As described in more detail below, the acquisition devices 12 acquire digital images of a patient and transmit the images to the editor 14. The editor 14 communicates with the controller 16 to manage the processing of acquired images, which includes storing the images in the image storage device 18. After the images are stored, a reviewer (e.g., an individual reviewing the acquired images for the clinical trial) can use a computing device executing a viewer application (hereinafter referred to as a "viewing device 26") to access stored images. Viewer applications are well-known in the medical image industry and are provided by numerous vendors. The available viewer applications provide different functionality and different compatibility with particular image storage devices 18. In some embodiments, the image storage device 18 includes a PACS, a RIS, and/or a clinical image management system ("CIMS"), which are well-known in the medical industry. Although illustrated as a single device, the image storage device 18 can include multiple devices (e.g., multiple servers or databases).

As illustrated in FIG. 1, a plurality of networks 20, 22, and 24 connect the acquisition devices 12, the editor 14, the controller 16, the image storage device 18, and the viewing device 26. The networks 20, 22, and 24 can include the Internet, a wide area-network ("WAN"), a local-area network ("LAN"), or combinations thereof. The networks 20, 22, and 24 can include wired connections, wireless connections, or combinations thereof. It should be understood that in some embodiments, two or more of the components can be combined into a single system and connected by internal connections as opposed to networks. For example, the controller 16, editor 14, image storage device 18, and viewing device 26 can be connected by internal connections to form a consolidated system for managing images without the need for networks 22 and 24.

Figure 2:
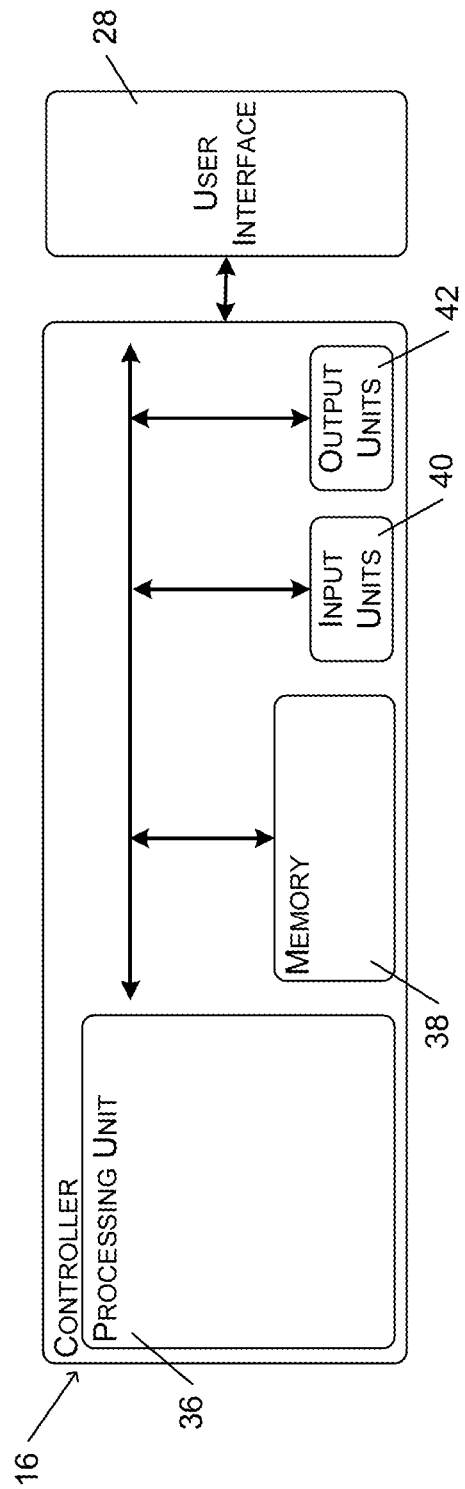
FIG. 2 illustrates a controller included in the digital image processing system of FIG. 1.

As illustrated in FIG. 2, the controller 16 includes at least one processing unit 36 (e.g., a microprocessor, a microcontroller, or another suitable programmable device), one or more non-transitory memory modules 38, one or more input units 40, and one or more output units 42. In some embodiments, the controller 16 includes a combined input/output module in addition to or in place of the separate modules 40 and 42. In addition, alternative configurations of the controller 16 are possible that include more, less, or different components.

The memory module 38 can include one or more types of memory, such as read-only memory ("ROM"), random access memory ("RAM"), flash memory, a hard disk, a removable drive, or other suitable magnetic, optical, physical, or electronic memory devices. As described in more detail below, the controller 16 is configured to retrieve instructions from memory 38 and execute the instructions to manage images. The instructions can include firmware, one or more applications, program data, filters, rules, one or more program modules, and other executable instructions. In some embodiments, the editor 14 is similarly implemented as a software-based device.

As illustrated in FIG. 2, the controller 16 communicates with a user interface 28. The user interface 28 can include a display and input devices such as a touch-screen, a keyboard, a mouse, a plurality of knobs, dials, switches, buttons, etc. As described in more detail below, a user can use the user interface 28 to configure the controller 16 and set parameters for how acquired images are managed and stored for a particular clinical trial.

It should be understood that the components of the system 10 can be combined and distributed in various configurations. For example, in some embodiments, the controller 16 can be combined with the editor 14. Furthermore, the controller 16 can be combined with other systems and devices commonly used in the medical industry, such as an electronic data capture system, a PACS, a RIS, a CIMS or a similar system used to store and manage patient information and subsequent access and processing. For example, in some embodiments, the controller 16 is combined with the image storage device 18, which includes a PACS, RIS, and/or CIMS.

Figure 3:
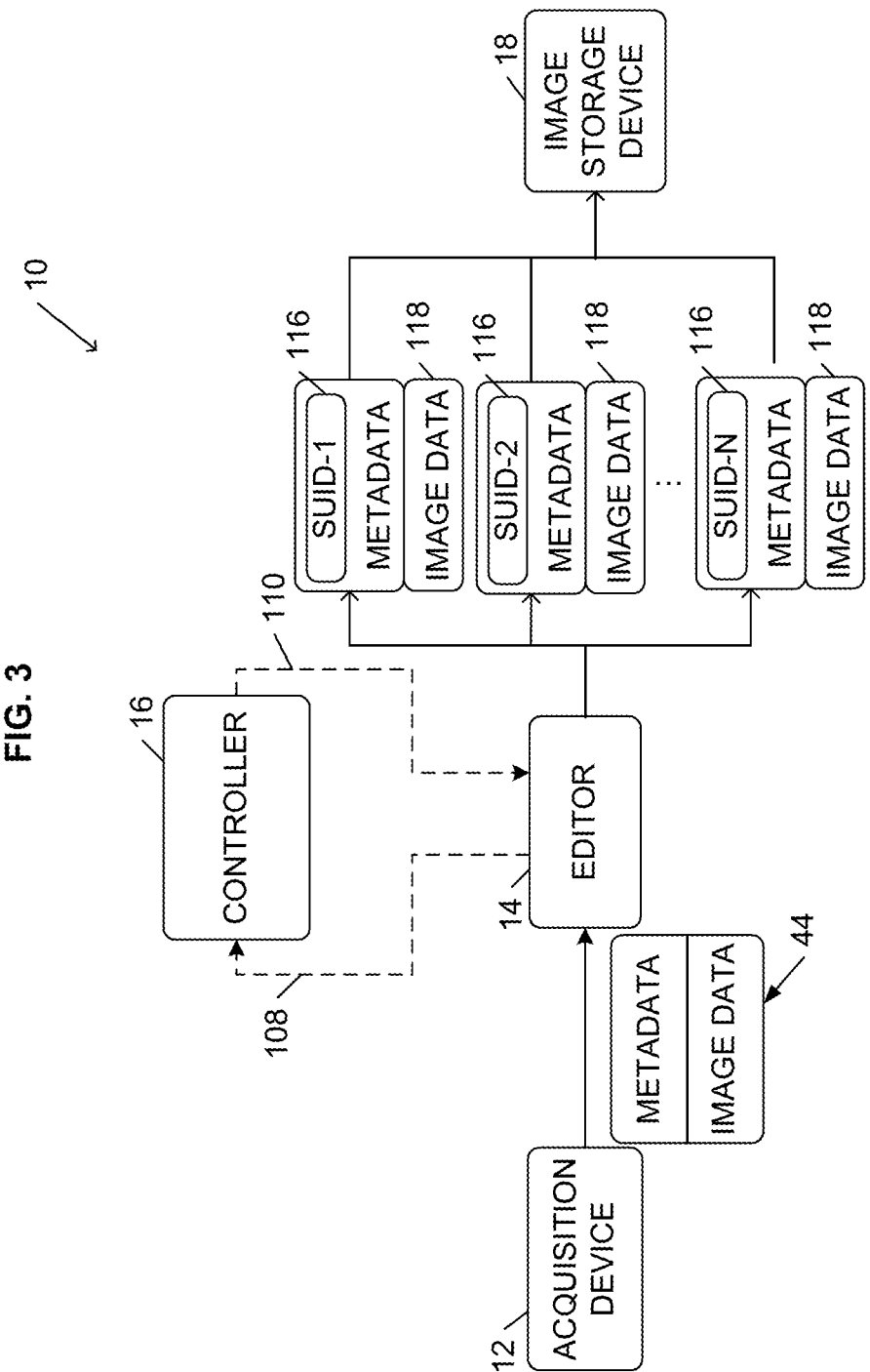
FIGS. 3 and 4 are flow charts illustrating methods performed by the digital image processing system of FIG. 1.

FIG. 3 illustrates a workflow performed by the system 10 for acquiring and managing images. As illustrated in FIG. 3, an acquisition device 12 acquires images and transmits an image object 44 to the editor 14. The image object 44 includes image data (i.e., the digital images captured during a radiological exam by the acquisition device 12) and metadata, which provides information regarding the image data (e.g., patient name, exam date, clinical trial identifier, etc.). In some embodiments, the metadata is contained in a header of the image data.

Figure 4:
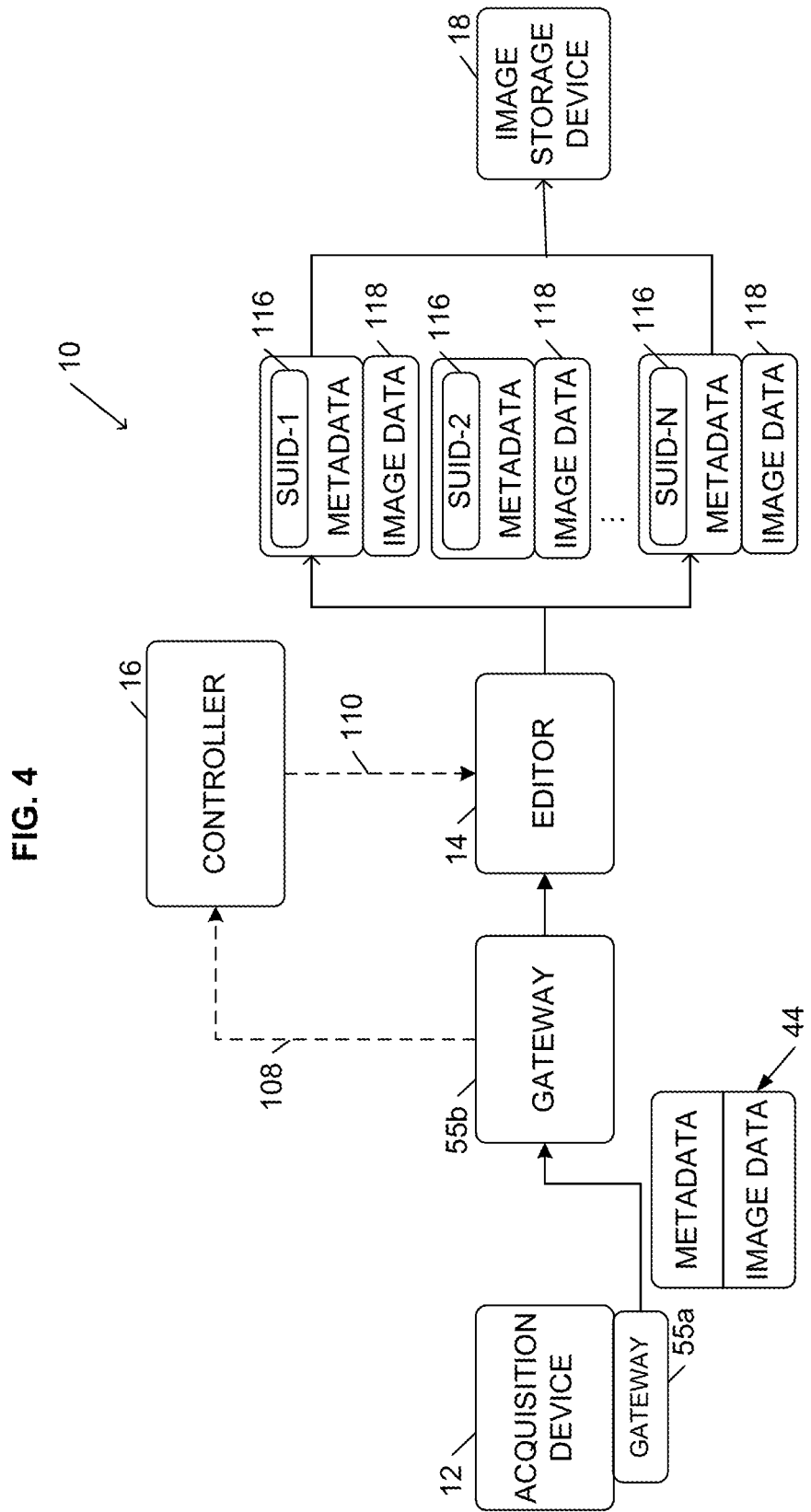

In some embodiments, the metadata is de-identified and standardized before it is transmitted to the editor 14 to comply with industry standards such as the Health Insurance Portability and Accountability Act ("HIPAA"). For example, if the editor 14 is located at a different location than the acquisition device 12, which requires that the image object 44 be transmitted over one or more public or non-secure networks, the acquisition device 12 can de-identify the metadata before transmitting the image object 44 to the editor 14 (e.g., using software installed at the acquisition device 12). In other embodiments, as illustrated in FIG. 4, the system 10 uses a gateway 55 to collect and coordinate the image object 44 to ensure that the image object 44 is compliant with industry standards and regulations (e.g., HIPAA) before the gateway 55 passes the object 44 to the editor 14 for additional processing. Gateways 55 are generally known in the art by various names such as an image gateway or image appliance, and are provided by a number of vendors including, for example, AG Mednet. A gateway can be implemented as an integrated hardware and software device or as a software-based device. For example, as illustrated in FIG. 4, a software-based gateway 55*a* ("a sending gateway") can be implemented at the acquisition site (e.g., as part of the acquisition device 12) to de-identify the image object 44 and send the image object 44, and a hardware and software gateway 55*b* ("a receiving gateway") can be implemented at the editor 14 (or as an intermediary device between the sending gateway 55*a* and the editor 14) to handle receipt of the image object 44. In addition to de-identifying the image object 44, a gateway 55 can provide data security, encrypt and de-crypt the image object 44, and/or compress and de-compress the image object 44. In some embodiments, if the editor 14 is located at or near the acquisition device 12 or the gateway 55, the editor 14 can be configured to perform the de-identification of the image object 44.

The editor 14 is a temporary repository of the image object 44. Once the image object 44 is received by the editor 14, the editor 14 communicates with the controller 16. For example, the editor 14 transmits one or more signals 108 to the controller 16 that notify the controller 16 that the editor 14 has received the image object 44. The signals 108 can include information regarding the received image object 44. For example, in some embodiments, the signals 108 include a clinical trial or subject identifier and other information included in the object's metadata.

Based on the signals 108, the controller 16 determines the clinical trial associated with the image object 44 and determines a number of copies of the image object 44 that is needed. The number of copies can correspond to the minimum number of independent reviewers (e.g., two) used in the determined clinical trial. In other embodiments, the number of copies corresponds to a maximum number of independent reviewers used (e.g., assuming that a tie-breaker may be needed).

To determine the number of copies needed, the controller 16 can access information (stored locally or on an external server or device) that specifies parameters for clinical trials. In some embodiments, a user inputs or sets the parameters for a particular clinical trial using the user interface 28 coupled to the controller 16. The parameters can include a number of independent reviewers (e.g., minimum or maximum) for a particular clinical trial. Upon receiving the parameters from the user through the user interface 28, the controller 16 stores the parameters (e.g., to one or more of the memory modules 38). Therefore, the controller 16 can use the clinical trial identifier included in the signals 108 to determine the clinical trial associated with the received images. The controller 16 can then access the parameters associated with the identified clinical trial to determine the number of copies of the image object 44 needed for the trial.

After determining the number of copies needed for the received image object 44, the controller 16 transmits one or more signals (e.g., processing instructions) 110 to the editor 14. The processing instructions 110 instruct the editor 14 to create a particular number of copies of the received image object 44. For example, the processing instructions 110 can include a number ("N") representing the number of copies needed for the image object 44. The processing instructions 110 can also include a unique identifier for each copy. In particular, to prevent the copies 118 from being exactly identical (which would causes access problems and errors if multiple image objects 44 were stored to the image storage device 18 with identical metadata), each copy 118 needs to be uniquely identifiable. For example, the metadata associated with each copy 118 needs to include at least one piece of information that is different from the metadata of the other copies 118. Therefore, the controller 16 can generate and provide the editor 14 (through the processing instructions 110) a unique identifier for each copy 118. As described below, the editor 14 can modify the metadata for each copy based on one of the unique identifiers provided by the controller 16. In some embodiments, the unique identifier is a value for at least one field included in the image object's header, such as a patient identification field, a medical record number field, a study universal identification number ("SUID") field, and/or an accession number field. It should be understood that the unique identifier can be the value of a single field or the combination of values of multiple fields. For example, the unique identifier can be a combination of the value of a trial identification field (similar to a patient identification field in a hospital setting) and the value of the medical record number field, SUID field, or accession number field.

Therefore, the editor 14 receives the processing instructions 110 and creates N copies 118 of the image object 44. The editor 14 also modifies the metadata associated with each copy 118 based on of the unique identifiers provided by the controller 16. For example, the metadata of each copy 118 includes at least one field 116, such as the SUID field illustrated in FIGS. 3 and 4, and the editor 14 sets the field 116 of each copy 118 to one of the unique identifiers provided by the controller 16. Accordingly, although each copy 118 includes most of the same data as included in the original image object 44 (e.g., the image data and metadata associated with administrative data, such as patient demographics, acquisition site information, etc.), each copy 118 is identifiable as a unique image object based on the information included in the field 116.

After creating the copies 118 and modifying the copies 118 based on the unique identifiers, the editor 14 transmits the copies 118 to the image storage device 18 for storage (e.g., as image objects 44). In some embodiments, the editor 14 discards the original image object 44 and does not transmit the original image object 44 to the image storage device 18. In other embodiments, the editor transmits the original image object 44 to the image storage device 18 with the copies 118 or transmits the original image object 44 to a second storage location separate from the image storage device 18. It should be understood that the functionality of the controller 16 and the editor 14 described above can be combined and distributed in various ways. For example, in some embodiments, the editor 14 generates the unique identifier for each copy 118 rather than the controller 16. In other embodiments, the controller 16 generates the copies 118 and supplies the copies 118 to the editor 14, and the editor 14 assigns the unique identifiers and stores the copies 118 to the image storage device 18. Furthermore, in some embodiments, the controller 16 is combined with the editor 14 and the functionality of each component as described above is provided by a single system or device.

Because the copies 118 have unique identifiers (e.g., field 116), the image storage device 18 stores and treats each copy 118 as a unique image object 44 (i.e., a unique study or exam) that can be independently accessed, and measurements, observations, and other annotations made to one copy 118 do not affect the other copies 118. Accordingly, the image storage device 18 can include standard, unmodified devices or products, such as a PACS, RIS, and/or CIMS, while still providing blind review for a clinical trial.

Although the image storage device 18 treats the copies 118 independently, the controller 16 can store information that associates the copies 118 with the original image object 44 (e.g., metadata from the original image object 44 and the unique identifiers assigned to the copies 118), such that the controller 16 can track the copies 118 made from the original image object 44. Accordingly, the controller 16 can provide information to individuals or other computing devices or systems regarding what image objects stored to the image storage device 18 are copies of the same original image object. This information can be used by the controller 16 or other computing devices or systems to reconcile assessments (e.g., compare independent assessments of images and request tie-breakers as needed). This information can also be used to alert particular reviewers when images are available for review. In particular, the controller 16 can provide a reviewer with a unique identifier associated with a particular image object stored in the image storage device 18 (e.g., a value for the field 116), and the reviewer can access the image from the image storage device 18 using the provided identifier and the viewing device 26. In some embodiments, the controller 16 can be configured to provide the unique identifier automatically to a particular reviewer. In other embodiments, the controller 16 can provide this information to individuals who manually inform the reviewers. In still other embodiments, the controller 16 can provide this information to other computing devices or systems that use the information to alert reviewers of available images.

Upon receiving a unique identifier for a stored image object, a reviewer can access the image object stored in the image storage device 18 using the viewing device 26. As noted above, because the image storage device 18 can include standard image management systems and devices, such as a RIS, PACS, and/or CIMS, the viewing device 26 can execute any standard viewer application compatible with the image storage device 18. Accordingly, the system 10 can be used to access images without requiring customized viewer applications.

Upon accessing an image object, the reviewer can provide measurements and annotations of the image data (hereinafter referred to as an "image assessment"). The image assessment can be saved with the image object in the image storage device 18. For example, in some embodiments, the image assessment is stored as part of the object's metadata. In other embodiments, the assessment is stored in a separate file, database, or server. However, even when the image assessment is stored separately from the image storage device 18, the assessment is linked to the associated object (e.g., based on the unique identifier included in the field 116 of the object). Therefore, the image assessment can be subsequently retrieved with the object.

Because each copy 118 is associated with a different unique identifier, even if one reviewer completes his or her review of their copy 118 in tandem with another reviewer, each reviewer is assessing a different copy 118. Furthermore, without having the unique identifiers of the other copies 118, each reviewer cannot access the assessments generated by the other reviewers of the other copies 118. Therefore, the reviewers remain blind to the assessments performed by other reviewers. The controller 16, however, retains the information necessary to link the copies 118 created for a particular original image object 44. The controller 16 can use this information to reconcile the independent assessments (e.g., compare the assessments to determine if a tie-breaker assessment is necessary) and manage review of each copy 118. It should be understood that the controller 16 can store the information necessary to link the copies 118 in the memory 38 or in a separate memory accessible by the controller 16 (e.g., over a direct connection or a network). Furthermore, in some embodiments, a component different from the controller 16 accesses the information linking the copies 118 and uses the information to reconcile the independent assessments or otherwise manage review of each copy 118.

In some embodiments, the system 10 also provides quality control to check for and correct various errors that can occur during a clinical trial. For example, in some cases an image object is received that uses various names for the same pathology or anatomy or an acquisition site sends too many series. In these cases, a quality control technologist would edit the exam or image object so that it complies with the clinical trial parameters. These changes need to be included in all of the copies created for the image object. If the quality control function takes place before the image object 44 reaches the editor 14, the editor 14 copies the image object 44 that already includes the quality control changes. Alternatively, if the quality control function takes place after the editor 14 copies the object, the editor 14 (based on information supplied from the controller 16) can update each of the previously-generated copes to include the quality control changes.

It should be understood that the components of the system 10 can be arranged in various configurations. For example, the editor 14 and the controller 16 can be included in the same location or alternatively, the controller 16 can be at a remote location with respect to the editor 14. Additionally, the editor 14 and the image storage device 18 can be included in the same location or alternatively, the image storage device 18 can be at a remote location with respect to the editor 14. Furthermore, as noted above, the system 10 may include a database or server other than the image storage device 18 to store image assessments. In addition, one or more of the above-described components can be hosted, such as in a "cloud" environment. For example, in some embodiments, the controller 16 is hosted but is configured to receive and provide information regarding acquired images and corresponding copies as described above. However, it should be understood that any combination of the components described herein may be hosted.

It should also be understood that, although systems and methods described herein are used in the context of managing medical images associated with a clinical trial, these systems and methods may be used for other applications. For example, the systems and methods described herein can be used in any application that requires independent blind or tandem review of images, such as for teaching or student evaluation purposes or for providing second opinions.

Thus, the invention provides, among other things, a system and method for creating and managing data objects that are independently retrievable for independent assessment. Various features and advantages of the invention are set forth in the following claims.

What is claimed is:

1. A method for managing at least one medical image, the at least one medical image including image data and metadata, the method comprising:
  determining, at a processor, a clinical trial associated with the at least one medical image;

accessing, at the processor, one or more parameters for the clinical trial, the one or more parameters including a number of independent reviewers used in the clinical trial;

generating, at the processor, a plurality of copies of the at least one medical image, a number of copies in the plurality of copies equal to the number of independent reviewers used in the clinical trial, each of the plurality of copies including the image data and the metadata;

after generating the plurality of copies and before making the plurality of copies accessible to a plurality of independent reviewers by storing the plurality of copies in at least one image storage device connected to one or more viewing devices via a network, modifying the metadata of each of the plurality of copies to include a unique identifier, the unique identifier being unique to each copy of the plurality of copies;

linking, at the processor, the unique identifier for each copy of the plurality of copies with the metadata from the at least one medical image to indicate which copies are generated based on the at least one medical image;

after modifying the metadata of each of the plurality of copies, storing the plurality of copies to the at least one image storage device for access by the plurality of independent reviewers via the network and automatically alerting an independent reviewer of the plurality of independent reviewers that a copy of the plurality of copies is ready for review;

receiving, from a user, one or more edits to an image object including the at least one medical image after generating the plurality of copies; and in response to receiving the one or more edits, updating each of the plurality of copies based on the one or more edits made to the image object including the at least one medical image and the metadata linking the unique identifier for each copy of the plurality of copies to the at least one medical image.

2. The method of claim 1, further comprising:
receiving, at a temporary repository, the image object including the at least one medical image,
once the image object is received at the temporary repository, transmitting, from the temporary repository, one or more signals associated with the at least one medical image, the one or more signals including a clinical trial identifier, and
receiving, at the processor included in a controller, the one or more signals,
wherein determining, at the processor included in the controller, the clinical trial associated with the at least one medical image includes determining the clinical trial associated with the at least one medical image based on the clinical trial identifier included in the one or more signals.

3. The method of claim 1, further comprising:
receiving, at a temporary repository, an image object including the at least one medical image,
transmitting, from the temporary repository, one or more signals associated with the at least one medical image, and
receiving, at the processor included in a controller, the one or more signals,
wherein determining, at the processor included in the controller, the clinical trial associated with the at least one medical image includes determining the clinical trial associated with the at least one medical image based on the one or more signals.

4. The method of claim 3, wherein generating the plurality of copies of the at least one medical image includes:
generating, at the processor, a plurality of unique identifiers, a number of the plurality of unique identifiers being equal to the number of copies;
transmitting, at the processor, one or more processing instructions to the temporary repository, the one or more processing instructions including the number of and the plurality of unique identifiers;
receiving, at the temporary repository, the one or more processing instructions; and
generating, at the temporary repository, the plurality of copies of the at least one medical image.

5. The method of claim 4, wherein modifying the metadata of each of the plurality of copies includes:
modifying, at the temporary repository, the metadata of each of the plurality of copies to include one of the plurality of unique identifiers included in the one or more processing instructions.

6. The method of claim 1, wherein modifying the metadata of each of the plurality of copies includes modifying at least one field included in the metadata of each copy of the plurality of copies to include a value different from a value of the at least one field in other copies of the plurality of copies.

7. The method of claim 6, wherein modifying the at least one field includes modifying a study universal identification field.

8. The method of claim 6, wherein modifying the at least one field includes modifying at least one of a patient identification field, a medical record number field, and an accession number field.

9. The method of claim 1, further comprising assigning the unique identifier of each copy of the plurality of copies to a different independent reviewer of the plurality of independent reviewers, each unique identifier allowing the respective independent reviewer of the plurality of independent reviewers to access and review one copy of the plurality of copies independently of remaining copies of the plurality of copies.

10. The method of claim 9, wherein alerting an independent reviewer of the plurality of independent reviewers that a copy of the plurality of copies is ready for review includes providing, to the independent reviewer, the unique identifier assigned to the independent reviewer.

11. The method of claim 1, further comprising accessing an image assessment associated with each copy of the plurality of copies and comparing the image assessments to determine when additional image assessments are needed.

12. The method of claim 1, the method further comprising:
standardizing metadata associated with the image object including the at least one medical image.

13. A method for managing at least one medical image, the at least one medical image including image data and metadata, the method comprising:
determining, at a processor, a clinical trial associated with the at least one medical image;
accessing, at the processor, one or more parameters for the clinical trial, the one or more parameters including a number of independent reviewers used in the clinical trial;
determining, at the processor based on the number of independent reviewers used in the clinical trial, a number of copies of the at least one medical image;

generating, at the processor, a plurality of unique identifiers, a number of the plurality of unique identifiers being equal to the number of copies;
generating a plurality of copies of the at least one medical image, a number of the plurality of copies being equal to the number of copies;
modifying the metadata of each of the plurality of copies to include one of the plurality of unique identifiers, the unique identifier being unique to each copy of the plurality of copies;
linking, at the processor, the unique identifier for each copy of the plurality of copies with the metadata from the at least one medical image to indicate which copies are generated based on the at least one medical image;
after modifying the metadata of each of the plurality of copies, storing the plurality of copies to at least one image storage device connected to one or more viewing devices via a network for access by a plurality of independent reviewers via the network and automatically alerting an independent reviewer of the plurality of independent reviewers that a copy of the plurality of copies is ready for review;
receiving, from a user, one or more edits to an image object including the at least one medical image after generating the plurality of copies; and
in response to receiving the one or more edits, updating each of the plurality of copies based on the one or more edits made to the image object including the at least one medical image and the metadata linking the unique identifier for each copy of the plurality of copies to the at least one medical image.

14. The method of claim 13, wherein determining the clinical trial associated with the at least one medical image includes determining the clinical trial based on a clinical trial identifier included in the metadata.

15. The method of claim 13, wherein modifying the metadata of each of the plurality of copies includes modifying at least one of a study universal identification field, a patient identification field, a medical record number field, and an accession number field.

16. The method of claim 13, further comprising assigning the unique identifier of each copy of the plurality of copies to a different independent reviewer of the plurality of independent reviewers, each unique identifier allowing the respective independent reviewer of the plurality of independent reviewers to access and review one copy of the plurality of copies independently of remaining copies of the plurality of copies.

17. The method of claim 16, further comprising accessing an image assessment associated with each copy of the plurality of copies and comparing the image assessments to determine when additional image assessments are needed.

18. The method of claim 13, wherein generating the plurality of copies includes instructing a second processor to generate the plurality of copies.

19. The method of claim 13, wherein modifying the metadata of each copy of the plurality of copies includes generating the unique identifier for each copy of the plurality of copies and instructing a second processor to modify the metadata of each copy of the plurality of copies based on the generated unique identifiers.

20. The method of claim 13, wherein storing the plurality of copies includes instructing a second processor to store the plurality of copies to the at least one image storage device.

* * * * *